United States Patent [19]

Tyndall

[11] Patent Number: 5,420,035

[45] Date of Patent: May 30, 1995

[54] BACTERIA ISOLATED FROM AMOEBAE/BACTERIA CONSORTIUM

[75] Inventor: Richard L. Tyndall, Clinton, Tenn.

[73] Assignee: Martin Marietta Energy Systems, Inc., Oak Ridge, Tenn.

[21] Appl. No.: 203,452

[22] Filed: Feb. 28, 1994

Related U.S. Application Data

[60] Division of Ser. No. 11,841, Feb. 1, 1993, Pat. No. 5,314,821, which is a continuation of Ser. No. 693,998, Apr. 26, 1991, abandoned.

[51] Int. Cl.[6] .................... C12N 1/12; C12N 1/20; F27D 3/00
[52] U.S. Cl. .................... 435/252.1; 435/252.4; 435/258.1; 435/243; 435/253.3
[58] Field of Search .................... 435/243, 252.1, 258.1, 435/252.4, 262.5, 947, 821, 261, 317.1, 253.3

[56] References Cited

U.S. PATENT DOCUMENTS

| | | | |
|---|---|---|---|
| 2,867,945 | 1/1959 | Gottas et al. | |
| 3,914,164 | 10/1975 | Clark | 204/149 |
| 4,127,447 | 11/1978 | Griffith et al. | 195/116 |
| 4,391,887 | 7/1983 | Baumgarten | 435/42 |
| 4,401,569 | 8/1983 | Jhaveri et al. | 210/610 |
| 4,447,541 | 5/1984 | Peterson | 435/264 |
| 4,511,657 | 4/1985 | Colaruotolo et al. | 435/253 |
| 4,535,061 | 8/1985 | Chakrabarty et al. | 435/253 |
| 4,664,805 | 5/1987 | Focht | 210/611 |
| 4,713,340 | 12/1987 | Crawford | 435/253 |
| 4,713,343 | 12/1987 | Wilson et al. | 435/264 |
| 4,737,461 | 4/1988 | Sugisawa et al. | 435/200 |
| 4,803,166 | 2/1989 | Kulpa et al. | 435/253.3 |
| 4,804,629 | 2/1989 | Roy | 435/253.3 |
| 4,816,403 | 3/1989 | Roy | 435/253.3 |
| 4,833,086 | 5/1989 | Horowitz | 435/252.1 |
| 4,853,334 | 8/1989 | Vanderbergh et al. | 435/262 |
| 4,859,594 | 8/1989 | Portier | 435/172.1 |
| 4,877,736 | 10/1989 | Fliermans | 435/183 |
| 5,314,821 | 5/1994 | Tyndall | 435/252.1 |

OTHER PUBLICATIONS

S. B. Garland et al., "The Use of Methanotrophic Bacteria for the Treatment of Groundwater Contaminated with Trichloroethene at the U.S. Department of Energy Kansas City Plant," ONRL/TM-11084, Nov. 1989, pp. 21, 41.

R. L. Tyndall et al., "Isolation of Amoebic-Bacterial Consortia Capable of Degrading Trichoroethylene," Twelfth Sym. on Biotech. for Fuels and Chemicals, May 7, 1990.

A. A. Vass et al., "Isolating Free Living Amoeba Can Select for Complex, Stable Consortia Capable of Degrading Toxins," ASM Int. Conf. on Multicellular Behavior of Bacteria, Oct. 21, 1990.

Stanier, et al., "The Microbial World", Prentice Hall, 1986, pp. 574–575.

Tyndall et al., "Free-Living Amoebae Used to Isolate Consorta Capable of Degrading Trichloroethylene", *Applied Biochemistry and Biotechnology*, vol. 28/29, 1991, pp. 917–925.

Hall, et al., Biosis Abstract 85:343756, 1985.

*Primary Examiner*—Michael G. Wityshyn
*Assistant Examiner*—T. J. Reardon
*Attorney, Agent, or Firm*—Joseph A. Marasco; Harold W. Adams

[57] ABSTRACT

New protozoan derived microbial consortia and method for their isolation are provided. Consortia and bacteria isolated therefrom are useful for treating wastes such as trichloroethylene and trinitrotoluene. Consortia, bacteria isolated therefrom, and dispersants isolated therefrom are useful for dispersing hydrocarbons such as oil, creosote, wax, and grease.

1 Claim, No Drawings

BACTERIA ISOLATED FROM AMOEBAE/BACTERIA CONSORTIUM

United States Government has rights in this invention pursuant to contract no. DE-AC05-84OR21400 between the United States Department of Energy and Martin Marietta Energy Systems, Inc.

CROSS REFERENCE TO RELATED APPLICATIONS

This application divisional application of application Ser. No. 08/011,841, filed on Feb. 1, 1993, issued as U.S. Pat. No. 5,314,821 on May 24, 1994, which is a continuation of application Ser. No. 07/693,998, filed Apr. 26, 1991, abandoned.

FIELD OF THE INVENTION

This invention relates to microbial consortia, and methods for altering or degrading wastes and contaminants. More particularly, this invention relates to protozoan derived consortia comprised of protozoa and bacteria, methods for isolating protozoa/bacteria consortia, methods for using protozoa/bacteria consortia for altering or degrading wastes and contaminants, and production and use of dispersants derived from protozoa/bacteria consortia.

BACKGROUND OF THE INVENTION

There is a need to alter or degrade solutions of waste and contaminants. In order to protect and remedy the increasingly polluted ecological sphere while continuing to make industrial and technological progress, it is necessary to provide effective means for altering or degrading chemical and biological wastes. To alter a substance is to chemically change the substance in some way; to degrade a substance is to alter the substance by breaking down the molecular structure thereof.

Trichloroethylene (TCE) is a prevalent chemical waste which has entered the environment at many Environmental Protection Agency (EPA) Superfund sites. These compounds are suspected carcinogens, and, being resistant to aerobic degradation, threaten water supplies.

Conventional techniques used to remedy contaminated sites are fraught with difficulty. Chemical treatment of high volume, contaminated water such as hexane extraction is not cost effective. Air stripping, while lower in cost, merely dilutes the pollutant into the air. Thus, an effective, low cost biological treatment method would be a significant step forward in remediation of contaminated sites. TCE is degraded by a variety of mechanisms. In anaerobic environments, TCE may be converted to more potent carcinogens such as vinyl chloride. TCE biodegradation by aerobic consortia or pure cultures of methanotrophs and pseudomonads has also been reported. Toluene dioxygenase enzyme from pseudomonads has been shown capable of TCE alteration, or degradation. However, either toluene or phenol was required. Other methanotrophic cultures can degrade TCE, apparently by the methane monoxygenase enzyme, without added toluene.

In various studies of biodegradation of a variety of toxic chemicals several problems were apparent. Some of the environments were apparently toxic to the test microbes or the chemicals were adsorbed to the soil particles and not available for degradation by the bacteria. Also, some soils contain extremely small particles, i.e. "fines" which prevent bacteria from penetrating between them and degrading the ensconced chemical(s).

Bacteria used to degrade TCE and other toxic chemicals are currently isolated directly from environmental sources.

OBJECTS OF THE INVENTION

Accordingly, it is an object of the present invention to provide new and useful microbial consortia.

It is another object of the present invention to provide new and improved methods for altering and degrading wastes and contaminants.

It is a further object of the present invention to provide new biologically derived compositions for chemically altering wastes and contaminants.

Further and other objects of the present invention will become apparent from the description contained herein.

SUMMARY OF THE INVENTION

In accordance with one aspect of the invention, a biologically pure strain of a microbe comprises a bacterium isolated from one of the following amoeba/bacteria consortia: ATCC 55120, ATCC 40908, ATCC 55342, ATCC 55343, a mutant of any one of these consortia possessing all the identifying characteristics thereof, and mixtures thereof. The microbes are identified as isolate 15, isolate 13, isolate 1s, isolate T, and isolate 9, and are fully characterized hereinbelow.

DETAILED DESCRIPTION OF THE PREFERRED EMBODIMENTS

Free-living amoebae populations were first isolated, and bacteria of interest were then subsequently isolated from the amoebae populations. The process of selecting initially for protozoa resulted in the isolation of microbial cultures capable of altering or degrading toxic or hazardous wastes. Some of the cultures produced dispersants.

Amoebae/bacteria consortia were discovered and isolated as follows. Water samples were obtained from several wells which were used to monitor a waste disposal site near Oak Ridge, Tenn. The test site was used previously for dumping of a variety of organic solvents including trichloroethylene (TCE). The number, depth, and approximate concentrations of TCE of the test wells were as follows: well 14, 13 ft., 2,100 ppb; well 27, 30 ft., 13,000 ppb; and well 46, 20 ft., 230 ppb. Water samples were aseptically collected by a nitrogen displacement sampling device (Well Wizard 3013; Q.E.D. Environmental Systems, Inc., Ann Arbor, Mich.). Samples were collected only after the well lines had been cleared through several cycles of pumping. The water samples were filtered through 1.2 μm cellulose nitrate-/acetate filters (Millipore Corp., Bedford, Mass.) which were then inverted and placed on mineral salts (NATE) agar. Prior to the addition of the filter pads, the plates were spread with a lawn of live *E. coli*. The test plates were incubated in air at room temperature (23°–25° C.) for 7–14 days. When amoebic outgrowths had migrated to the edge of the petri dishes the plates were transferred to desiccator jars flushed with 10% methane in air. The resultant microbial consortia, given identification numbers 14, 27b, 27p and 46, appeared after 2 weeks in the methane atmosphere along the area of amoebic outgrowth. The consortia were aseptically transferred every 3–4 weeks onto NATE agar media plates incubated in a methane in air atmosphere. Heterotrophic bacteria from the consortia were isolated and maintained at room temperature on trypticase soy agar (TSA).

Water from all three test wells yielded free-living amoebae on the NATE plates spread with *E. coli* as a food source. Bacterial growth occurred in the methane atmosphere along the area of amoebic migration, demonstrating that amoebae could harbor methanotrophic bacteria. Control plates without *E. coli*, which allows for amoebic migration, did not support methanotrophic growth away from the filter. Bacterial growth subsequently occurred on transfer of the amoebic populations to fresh NATE plates without added *E. coli* in a methane atmosphere. These consortia can apparently be maintained indefinitely by subculture on NATE in a methane atmosphere.

Individual components of the consortia were isolated and characterized. Heterotrophic and methanotrophic bacteria and amoebae continually coexist in the consortia. Microscopic examination of the amoebic trophozoites and cysts indicated they were Hartmannella. The presence of heterotrophs in these consortia grown in a methane atmosphere was evident on transfer of aliquots from NATE to TSA. Microscopic and enzymatic analysis showed the resultant heterotrophic populations were a mixture of genera, including but not limited to Pseudomonas, Alcaligenes, Bacillus, Moraxella, Cytophaga, Paracoccus and Hyphomicrobium, as shown in Tables 1, 2, and 3.

When suspensions of the consortia were filtered through a 0.8 μm filter and the flitrate subcultured three times on TSA the resultant heterotrophs could no longer grow when replated on NATE in a methane in air atmosphere. Conversely, when amoebic populations from the NATE plates in a methane atmosphere were subcultured three times in air on nonnutrient agar spread with a lawn of live *E. coli* (NNAE) plates and the newly generated peripheral amoebic populations were replated on NATE in methane, bacterial growth—presumably methanotrophs—sometimes reoccurred. In addition, when amoebic populations grown on NNAE plates were stored for several weeks such that encystation occurred, viable methanotrophic and heterotrophic bacteria were still present as evident from colony growth when the amoebic cysts were transferred to NATE media in a methane atmosphere. When consortia, maintained on NATE in methane and air, were filtered through 0.8 μm filters and the flitrate replated on NATE in methane, methanotrophic and heterotrophic colonies free of detectable amoebae were occasionally obtained.

Thus, we have been able to free heterotrophic bacteria from methanotrophic bacteria and amoebae and have been able to free the amoebae from methanotrophic and heterotrophic bacteria. We have not as yet, however, been able to disassociate the methanotrophic from the heterotrophic bacteria following separation from the amoebae.

TABLE 1

Characterization of Bacteria from Consortium 14

| Possible Identification | Growth on Methane as Sole Carbon | Unique Characteristics |
|---|---|---|
| Pseudomonas sp. | + | Catalase 3+ |
| Pseudomonas sp. | + | — |
| Bacillus sp. | + | Gelatin + |
| Acinetobacter sp. | + | — |
| Bacillus sp. | — | Orange pigmentation |

TABLE 1-continued

Characterization of Bacteria from Consortium 14

| Possible Identification | Growth on Methane as Sole Carbon | Unique Characteristics |
|---|---|---|
| Acinetobacter sp. | — | — |

TABLE 2

Characterization of Bacteria from Consortium P27

| Possible Identification | Growth on Methane as Sole Carbon | Unique Characteristics |
|---|---|---|
| Pseudomonas sp. | + | Catalase 3+ |
| Pseudomonas sp. | + | — |
| Bacillus sp. | — | Orange pigmentation |
| Bacillus sp. | + | Gelatin + |
| Acinetobacter sp. | — | — |
| Pseudomonas sp. | — | — |
| Xanthomonas sp. | — | Oxidase — |

TABLE 3

Characterization of Bacteria from Consortium 46

| Possible Identification | Growth on Methane as Sole Carbon | Unique Characteristics |
|---|---|---|
| Pseudomonas sp. | + | — |
| Paracoccus sp. | — | ONPG + |
| Pseudomonas sp. | + | Vacuoles |
| Moraxella sp. | + | ONPG + |
| Pseudomonas sp. | + | Nitrate + |
| Cytophaga sp. | + | Corrodes Agar (Possibly breaks C-C bonds) |
| Pseudomonas sp. | + | — |
| Pseudomonas sp. | — | — |
| Pseudomonas sp. | — | — |
| Alcaligenes sp. | — | Citrate + |
| Hyphomicrobium sp. | | |

Electron microscopic examination of the consortia and the methanotroph/heterotroph mixture showed no evidence of a Type I methanotroph which had been previously isolated from the aforementioned site. Instead, examination of the methanotroph/heterotroph mixture showed some bacteria with typical gram-negative morphology and many cells with morphologic characteristics of Hyphomicrobium. Typical free-living amoebae with the expected "bulls-eye" nucleolus were evident. Bacteria were commonly seen in the amoebic cytoplasm both in the trophozoite and cyst stage. In both conditions the bacteria were in membrane bound vacuoles.

The nature of these stable amoebae/bacteria associations appear to be somewhat symbiotic, indicated by the continuing presence of both amoebae and heterotrophs on a minimal salts medium in a methane/air atmosphere. Neither heterotrophs nor amoebae alone are generally believed to persist under these conditions. Indeed, the heterotrophs and amoebae isolated from the consortia could no longer grow under such conditions. The most likely explanation of the stability of the amoebic-bacteria consortia on NATE in a methane atmosphere is the growth of the methanotrophic bacteria allowing the persistence of the amoebae and heterotrophs.

The electron microscopic examination of the consortia and methanotroph/heterotroph mixtures also helped explain some of the cultural observations and difficulties. In light of the observed intra-amoebic presence of bacteria, it is seen why the initial isolation of amoebic cultures yielded bacterial isolates on subsequent transfer of the amoebae to a methane in air environment. It also explains the difficulties in trying to free the amoebae of the methanotrophs and heterotrophs. Similarly, the difficult, and as yet unrealized, separation of methanotrophs and heterotrophs is likely explained by the abundance of Hyphomicrobium which most likely makes up the majority of the bacterial component. This genera of microorganism is noted for its proclivity for associating with other microorganisms such that their isolation in pure culture has been rarely attained. Hyphomicrobium can grow in the presence of single-carbon sources and mineral salts as used herein. They can be found in association with methanotrophs and may degrade methanol produced by methanotrophs, preventing the toxic accumulation of methanol. Whether the Hyphomicrobium degrade TCE is not presently testable since we have not as yet separated them from the other bacteria in spite of trying density gradients and other techniques.

The amoebae in the trophozoite or cyst form may provide a more stable niche for the metabolic activities of the associated methanotrophs and heterotrophs. For instance, the ability of free-living amoebae to protect associated bacteria from the killing effects of chlorine has been demonstrated. Thus, the isolation of the methanotrophs from encysted and subsequently excysted amoebae may be pertinent.

Type I methanotrophs could not be identified by either electron microscopy or by culture from the amoebae/bacteria consortia described herein. However, degradation of TCE by the total consortia, but not by heterotrophs or amoebae populations per se, suggests the methanotrophic bacteria are the TCE-degrading component of the consortia. Unlike the degradation of TCE by Type I methanotroph isolated by from the same site, a greater proportion of the $^{14}C$ was found in $CO_2$ as opposed to cellular and soluble fractions when TCE was degraded by the consortia described herein.

EXAMPLE I

The ability of the consortia to degrade TCE in a methane atmosphere was tested. The microorganisms were incubated in 100 mL of liquid NATE medium in 250 mL bottles fitted with teflon septa. The test bottles were injected with 12 mL of filtered sterilized methane (0.536 mmol) in 150 mL of headspace volume. They were supplemented with [1,2-$^{14}C$] trichloroethylene (3.0 mCi/mmol [111 MBq/mmol], 95% pure by GC, Pathfinder Laboratories, St. Louis, Mo.). The test bottles were inverted and incubated for 12-14 days at 22°-24° C. on a shaker platform. The contents were analyzed for TCE periodically. Autoclaved cultures were used as negative controls. Other controls included incubating cultures in air without methane and testing of E. coli in place of the consortia. After incubation, the content of $^{14}C$-TCE in cellular material, $CO_2$, and culture fluid was determined by conventional scintillation techniques. TCE was degraded by the various consortia as indicated in the fate of $^{14}C$-labelled TCE exposed to the consortia in a methane in air atmosphere, shown in Table 4.

TABLE 4

Degradation of $^{14}C$-Trichloroethylene (TCE) by Microbial Consortia
Average percent $^{14}C$ per fraction[b]

| Consortia[a] | No. of Expts. | Cell Pellet | $CO_2$ | Soluble |
|---|---|---|---|---|
| 14 | 2 | 13(0–25) | 87(75–100) | 0 |
| 27B | 3 | 11(6–16) | 49(25–89) | 40(0–69) |
| 27P | 2 | 11 | 73(57–89) | 16(0–32) |

TABLE 4-continued

Degradation of $^{14}C$-Trichloroethylene (TCE) by Microbial Consortia
Average percent $^{14}C$ per fraction[b]

| Consortia[a] | No. of Expts. | Cell Pellet | $CO_2$ | Soluble |
|---|---|---|---|---|
| 46 | 5 | 10(0–19) | 75(50–100) | 15(0–37) |

[a]Numerical designation indicates well water of origin.
[b]Determined after subtracting E. coli or autoclaved controls which were about 10% of that observed with consortia. Percent of $^{14}C$-TCE degraded by the consortia ranged from 30–40% after 12 days incubation at 25° C.

EXAMPLE II

Amoebae and bacterial heterotrophs from the consortia were tested for and found not to have ability to degrade TCE. Mixtures of methanotrophic and heterotrophic bacteria isolated from the consortia degraded TCE. Neither the heterotrophic bacteria nor amoebae population without associated methanotrophic bacteria degraded TCE. Trichloroethylene was not appreciably degraded by consortia or methanotrophs in air. Neither autoclaved consortia nor E. coli degraded appreciable amounts of $^{14}C$-TCE. Results are shown in Table 5.

TABLE 5

Degradation of $^{14}C$-Trichloroethylene (TCE) by Components of Microbial Consortia
Counts of $^{14}C$ per Fraction[a]

| Consortium Component | No. of Expts. | Cell Pellet | $CO_2$ | Soluble |
|---|---|---|---|---|
| Original consortium | 2 | 656 | 2844 | 2010 |
| Methanotrophs/ Heterotrophs[b] | 2 | 854 | 3037 | 2185 |
| Amoebae[c] | 2 | 142 | 145 | 570 |
| Heterotrophs[d] | 2 | 129 | 105 | 600 |
| E. coli control | 2 | 129 | 113 | 550 |

[a]Average total counts added to test system was 12,875. Consortia, amoebae, methanotrophs and heterotrophs incubated with TCE in air in the absence of methane showed counts similar to E. coli control.
[b]The original consortium was filtered through a 0.8 μm filter and passaged three times on a mineral salts media in a methane in air atmosphere. When the resultant microbial growth was tested for amoebae and heterotrophs no amoebae were detected but heterotrophs were still present.
[c]Amoebae were passaged three times on nonnutrient agar spread with a lawn of E. coli. When replanted on mineral salts in a methane atmosphere no bacterial growth was apparent.
[d]Heterotrophs were passaged three times on TSA and were free of amoebae and methanotrophs.

Because of the successful degradation of TCE by two of the bacteria/amoebic consortia (27P, 46), these consortia were also tested for their ability to alter or degrade 2,4,6 trinitrotoluene

EXAMPLE III

Sterile NATE solution was mixed in equal volume with a saturated TNT solution (100mg/L) for a total volume of 100 ml and inoculated with $10^{12}$ organisms. This was done in 250 ml teflon sealed bottles with 15 ml of methane added to the headspace through the teflon septa. These bottles were tested under the following conditions: 46 consortium+methane, 46 consortium−methane, 27p consortium+methane, 27p consortium−methane, TNT solution+methane (no bacteria) and TNT solution (no methane, no bacteria).

No visible differences were seen in any of the bottles except for the 46 consortium with methane in which the liquid medium turned yellow. The color change occurred rapidly (overnight) on approximately Day 12 in repeat experiments. The media from each bottle was analyzed by high pressure liquid chromatography (HPLC) after 3 weeks incubation; the 46 consortium under methane showed a decrease in TNT levels.

EXAMPLE IV

In an experiment similar to Example III using $^{14}C$-labeled TNT, the $^{14}C$-TNT was associated with the cell pellet, and was not extractable with acetonitrile (unlike the other bottles). This suggests that the TNT is tightly associated with the cell, or has become nonpolar since TNT and its metabolites are readily extractable with acetonitrile. Table 6 shows that "altered" TNT is, in fact, associated with the cell pellet and has not been degraded to carbon dioxide nor remained in the supernate.

TABLE 6

| $^{14}C$-TNT Alteration by 46 Consortium | | | |
|---|---|---|---|
|  | Bottle #1 | Bottle #2 | Control |
| $^{14}CO_2$ | 1.5% | 1.9% | 4.1% |
| $^{14}$TNT in supernate | 28.9% | 31.7% | 89.8% |
| $^{14}$TNT in cell pellet | 69.6% | 66.4% | 3.5% |

An organism from Consortium 46, *Cytophaga sp.*, was observed to decompose agar (ie. break C—C bonds), prompting experiments to test isolated organisms' ability to alter, degrade, or disperse C—C based hydrocarbons, especially nonpolar substances such as creosote, oil, wax and grease. Oil, creosote, wax, and grease can be dispersed into microdroplets in order to facilitate degradation by consortia, additional organisms, or other methods or natural processes.

EXAMPLE V

Dilute suspensions of each organism in Consortium 46 were placed, respectively, in 100 ml saline with 0.1 gm of creosote, and in 100ml saline with 0.1 gm of crude oil. Five organisms were found to have the ability to immediately disperse the creosote and crude oil into microdroplets. It was found that the five organisms represented two different modes of action. Two of the bacteria, isolates T and 9, were found to have this ability only if the cells were present. The other three organisms, isolates 13, 15, and 1s, were found to produce a dispersant which produced the dispersion effect. In all cases the dispersant was more effective after autoclaving and resultant sterilization. Each dispersant greatly reduced the liquid interstitial surface tension, indicated by tensiometer tests. Samples of wax and grease were also dispersed. Isolate 13 was found to be especially effective in dispersing wax.

EXAMPLE VI

The bacterial isolates described in Example V were tested on wood contaminated with creosote, resulting in obvious desorption of creosote from the wood.

Soil fines, postulated to hinder decomposition of contaminating substances by creating pockets which can not be reached by bacteria or fungi, can be eliminated.

EXAMPLE VII

The bacterial isolates described in Example V were tested on soil contaminated with creosote. The dispersants altered the physical nature of the soils by virtually eliminating the fines, or very fine particulate matter.

Additional testing with various organic compounds such as nicotine showed that the dispersant allowed maximal extraction in a much shorter time frame than expected, because of its ability to microemulsify nonpolar organic compounds.

Preliminary analysis by column chromatography and concentration procedures showed that the dispersant produced was slightly different in each bacteria (different molecular weights and effectiveness). Each dispersant appears to have a negative charge associated with at least a part of the molecular structure. The dispersants are assumed to be partly denatured protein and possibly partly lipid in nature since lipase can significantly reduce their effectiveness. These appear to be the first bacterially produced dispersants or microemulsifiers known to exist.

Optimization of growth conditions for three of the five organisms has been performed and these organisms can be rapidly grown on standard microbiological media under slightly different temperatures and pH conditions.

Many types of bacteria have also been found to be able to use these products as a nutrient base which has the added advantage of not only dispersing C—C based compounds, but simultaneously fertilizing the indigenous flora which could facilitate decomposition.

Additionally, it has been found that all organisms isolated from the consortia which can disperse oil, creosote, wax, and grease also have the ability to precipitate iron added to the growth medium.

Bacteria capable of dispersing oil, creosote, wax, and grease were characterized as follows:

Isolate 15: Family Pseudomonadaceae, Genus Pseudomonas Species probably *pseudoalcaligenes*: Gram negative rod, 0.5–1.5 $\mu$m. Oxidase negative, catalase positive, motile, non sporulating, TSI (K/−). Colony morphology on Tryptic Soy Agar media—translucent, undulate, diffuse margins, mucoid, pale white—yellow green. Produces green diffusible pigment on Mueller-Hinton agar with grape-like odor. Colonies on BCYE medium have irregular margins are mucoid and yellow-white. Aerobic, but grows weakly in methane atmosphere as sole carbon source. Can use the following carbon sources for growth and metabolism: tween 40, tween 80, N-acetyl-D-glucosamine, L-arabinose, D-arabitol, D-fructose, D-galactose, D-mannitol, D-mannose, D-trehalose, methyl pyruvate, mono-methyl succinate, acetic, formic, citric, lactic, valetic, propionic and succinic acids, glycerol, serine, ornithine, leucine, histidine and alanine. ONPG, VP, nitrate reduction and gelatine negative. Does not possess arginine dihydrolase, lysine decarboxylase, urease, tryptophane deaminase or ornithine decarboxylase. Hydrogen sulfide is not produced. Optimum temperature and pH for growth are 20° C. and 7.0, respectively.

Isolate 13: Family (uncertain), Genus Alcaligenes, Species (unknown): Gram negative rod, 0.5–1.5 $\mu$m. Oxidase positive, catalase positive, motile, non sporulating, TSI (K/−). Colony morphology on Tryptic Soy Agar media—opaque, entire, dry, off-white with a musty odor. Growth on Mueller-Hinton agar is sparse with small colonies that are translucent, entire and pale yellow. On BCYE medium the colonies are small, entire, pale-yellow with a musty odor. Aerobic—does not grow in methane atmosphere as sole carbon source. Can use the following carbon sources for growth and metabolism: tween 40, tween 80, L-arabinose, psicose, D-fructose, methyl pyruvate, mono-methyl succinate, acetic, gluconic, formic, citric, lactic, valerie, propionic and succinie acids, glycerol, serine, leucine, histidine and alanine. ONPG, VP, nitrate reduction and gelatine negative. Does not possess arginine dihydrolase, lysine decarboxylase, urease, tryptophane deaminase or ornithine decarboxylase. Hydrogen sulfide is not produced. Citrate positive. Optimum temperature and pH for growth are 25° C. and 7.5, respectively.

Isolate Is: Family Pseudomonadaceae, Genus Pseudornonas, Species (unknown): Gram negative rod, 0.5–1.5 μm. Oxidase positive, catalase positive, motile, non sporulating, TSI (K/−). Colony morphology on Tryptic Soy Agar, BCYE and Mueller-Hinton—translucent, entire, mucoid, pale white to yellow with a faint grape-like odor. Aerobic, but grows weakly in methane atmosphere as sole carbon source. Can use the following carbon sources for growth and metabolism: tween 40, tween 80, N-acetyl-D-glucosamine, L-arabinose, methyl pyruvate, mono-methyl succinate, acetic, citric, itaconic, glutaric, lactic, propionic, sebacic, aspartic and succinic acids, L-proline, L-phenyl alaninc and phenyl ethylamine. ONPG, VP, nitrate reduction and gelatine negative. Does not possess arginine dihydrolase, lysine decarboxylase, urease, tryptophane deaminase or ornithine decarboxylase. Hydrogen sulfide is not produced. Optimum temperature and pH for growth are 25° C. and 7.0, respectively.

Isolate T: Family Neisseriaceae, Genus Acinetobacter, Species (unknown): Gram negative coccobacillus, 0.5–1.0 μm. Oxidase negative, catalase positive, non motile, non sporulating, TSI (K/−). Colony morphology on Tryptic Soy Agar media—opaque, entire, dry, white. Aerobic, but grows weakly in methane atmosphere as sole carbon source. ONPG, VP, nitrate reduction and gelatine negative. Does not possess arginine dihydrolase, lysine decarboxylase, urease, tryptophane deaminase or ornithine decarboxylase. Hydrogen sulfide is not produced. Optimum temperature and pH for growth are 25° C. and 7.0, respectively.

Isolate 9: Family Pseudomonadaceae, Genus Pseudomonas, Species (unknown): Gram negative rod, 0.5–1.5 μm. Oxidase negative, catalase positive, motile, non sporulating, TSI (K/−). Colony morphology on Tryptic Soy Agar media—opaque, entire, dry, yellow. Aerobic, but grows weakly in methane atmosphere as sole carbon source. ONPG, VP, nitrate reduction and gelatine negative. Does not possess arginine dihydrolase, lysine decarboxylase, urease, tryptophane deaminase or ornithine decarboxylase. Hydrogen sulfide is not produced. Optimum temperature and pH for growth are 25° C. and 7.0, respectively.

Some of the bacterial isolates from the consortium showed antibiotic (antimicrobial and/or antifungal) activity.

EXAMPLE VIII

Tests were carried out using a standard double blind protocol wherein isolates inhibited fungal growth in liquid media. In this protocol, individual bacteria from the consortia and various, unidentified test fungi were placed together in dilute media concentrations in the wells of a microtiter plate. The microtiter plate was incubated for one week and then examined microscopically for the presence of either bacteria, fungi or both. Control wells established the viability of all organisms. Fungi were not amoeba derived and represented common environmental fungi; therefore bacterial inhibition of the fungi is stressed as an important advantage of the present invention. If bacteria were present and no fungi grew, this was interpreted as the bacteria possessing an antifungal agent. If fungi were present and no bacteria, this was interpreted as the fungi possessing an antibacterial agent. If both bacteria and fungi were present, no antibiotic effects were detected. Since the bacteria were originally amoeba associated, a contribution of the amoeba to antimicrobial activity of the bacteria cannot be ruled out. Results are shown in Table 7.

TABLE 7

| | Bacterial isolates from consortia 46 and 27P | | | | | | | | | | | | | | | | | | | | | | |
|---|---|---|---|---|---|---|---|---|---|---|---|---|---|---|---|---|---|---|---|---|---|---|---|
| | A | B | C | D1 | D2 | G | H | I | K1 | K2 | L1 | M | N | O | P1 | P2 | Q | R | S | T | AF | 1S | 13 |
| FUNGUS 1 | − | − | − | − | − | − | − | − | − | − | − | − | − | − | − | − | − | − | − | − | − | − | − |
| 2 | # | # | # | − | − | − | # | # | − | − | − | − | − | − | − | − | − | − | # | − | − | − | − |
| 3 | # | # | # | − | − | − | # | # | − | − | − | − | − | − | − | − | − | − | # | − | − | − | − |
| 4 | − | − | # | − | − | + | # | − | + | + | + | + | + | + | + | − | + | # | − | − | + | + | + |
| 5 | − | − | # | + | − | + | − | − | + | + | + | + | + | + | + | + | + | # | − | − | + | + | + |
| 6 | − | − | − | − | − | − | − | − | − | − | − | − | − | − | − | − | − | # | # | − | − | − | − |
| 7 | − | − | − | − | − | − | − | − | − | − | − | − | − | − | − | − | − | − | − | − | + | − | − |
| 8 | − | − | − | − | − | − | − | − | − | − | − | − | − | − | − | − | − | − | − | − | − | + | − |
| 9 | − | − | − | − | − | − | − | − | + | + | + | − | − | − | − | − | − | − | − | − | − | − | − |

+ bacteria inhibited fungus
fungus inhibited bacteria
− indicates no effect on either bacteria or fungus Based on the ability of these consortia to degrade, disperse or alter various compounds, these protozoan derived consortia are useful for bioremediation efforts. Pathogenicity testing of these consortia showed that no known pathogens are present, enhancing their usefulness.

Bioremediation is generally carried out by utilizing conventional methods. These include the use of bioreactors, and fertilization or composting, allowing indigenous organisms to remove the contaminants. The subject consortia can be utilized whole or in part for these methods.

Bioreactors are typically placed on-site and require moving contaminated material from the site of contamination to the bioreactor for processing. The bioreactor itself can consist of various shapes and sizes but is typically a cylinder which is filled with inert material which bacteria can attach to. As the contaminated material is added to the reactor, the large surface area created by the inert material allows maximal contact of the contaminant with the bacteria responsible for degrading it. Our consortia are ideally suited for this type of remediation and can be added directly onto the inert material. Concentrations which would be effective range from $1 \times 10^{10}$ to $1 \times 10^{12}$ organisms per liter of bioreactor surface area.

Fertilization typically entails adding compounds (nitrogen, phosphate) to contaminated soils or other contaminated substances in order to stimulate indigenous organisms which may be capable of degrading the contaminant to less hazards concentrations or altering it to non-toxic forms. This is usually performed over large areas at the site of contamination and is usually sprayed over the area so that it soaks into the ground. This process, without the addition of degrading bacteria, typically requires long time periods and is not totally effective. Addition of our consortia would enhance this procedure since fertilization may also stimulate some of the components of our consortia as well as indigenous organisms. Also, the dispersants produced by the consortia may help in desorbing some contaminants and, by eliminating soil fines, should enhance the degradative ability of both indigenous and added microbes. Our consortia could yield itself quite readily to this type of bioremediation and could be added directly to the fertilizer if the concentrations are not too high. Effective concentrations would range from $1\times10^{10}$ to $1\times10^{12}$ organisms per liter of spray solution.

From years of manufacturing and handling of explosive materials at U.S. Army facilities, over 1,000,000 cubic yards of soil and sediments have become contaminated with TNT and other explosives. The only available remedial option is incineration which can be very expensive. Composting is currently being tested as an alternative remediation technology when incineration is ruled out. This is accomplished by mixing contaminated soil with manure, wood chips, hay, fertilizer and other amendments, creating a favorable environment for the indigenous microbes (from the contaminated soils) enabling them to mineralize the explosives. Addition of our consortia to such a procedure would also supplement and increase the rate at which these compounds are degraded. It could also begin alteration of TNT before indigenous organisms increase to such an extent as to be useful. In addition, alteration of TNT by consortia 46, could produce metabolites which are more easily degraded than TNT by other organisms. As previously discussed, the desorption of contaminants afford the elimination of soil fines could enhance the reaction. Effective concentrations would range from $1\times10^{10}$ to $1\times10^{12}$ organisms per kilogram of compost.

Deposit of Microorganisms

The applicant, in accordance with the provisions of the Budapest treaty on the international recognition of the deposit of microorganisms for the purposes of patent procedure, did deposit samples of consortia 46 and *27b*, *27p* with the American Type Culture Collection (ATCC), 12301 Parklawn Drive, Rockville, Md. 20852, U.S.A. Consortium 46 was deposited with the ATCC on Oct. 11, 1990 and assigned ATCC deposit reference No. 40908. Consortium *27p* was deposited with the ATCC on Nov. 8, 1990 and assigned ATCC deposit reference No. 55120. Consortium *27b* was deposited with the ATCC on Jul. 16, 1992 and assigned ATCC deposit reference No. 55343. Consortium 14 was deposited with the ATCC on Jul. 16, 1992 and assigned ATCC deposit reference No. 55342.

While there has been shown and described what is at present considered the preferred embodiment of the invention, it will be obvious to those skilled in the art that various changes and modifications may be made therein without departing from the scope of the invention as defined by the appended claims.

We claim:

1. A biologically pure strain of a microbe comprising a heterotrophic bacterium isolated from an amoeba/-bacteria consortium consisting of ATCC 40908, or a mutant of said consortium possessing all the identifying characteristics of said consortium, said bacterium selected from the group consisting of ATCC 75527, ATCC 75529, ATCC 55638, ATCC 55639, and ATCC 55640.

* * * * *